United States Patent
Furman et al.

(10) Patent No.: US 6,194,481 B1
(45) Date of Patent: Feb. 27, 2001

(54) MECHANICALLY STRONG AND TRANSPARENT OR TRANSLUCENT COMPOSITES MADE USING ZIRCONIUM OXIDE NANOPARTICLES

(75) Inventors: Benjamin R. Furman; Stephen T. Wellinghoff; Henry R. Rawls; Hong Dixon; Barry K. Norling, all of San Antonio, TX (US)

(73) Assignees: Board of Regents of the University of Texas System, Austin; Southwest Research Institute, San Antonio, both of TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/314,350

(22) Filed: May 19, 1999

(51) Int. Cl.$^7$ .............................. C08K 3/22; C08K 9/06; C08F 2/50
(52) U.S. Cl. ............................. 522/77; 522/81; 522/83; 522/79; 522/71; 522/103; 522/182; 522/908; 523/115; 523/116; 524/398; 524/413
(58) Field of Search ................................. 522/81, 83, 77, 522/79, 71, 908, 103, 182; 523/115, 116; 524/413, 398

(56) References Cited

U.S. PATENT DOCUMENTS

| 4,215,033 | | 7/1980 | Bowen . |
|---|---|---|---|
| 4,539,048 | * | 9/1985 | Cohen . |
| 4,623,738 | * | 11/1986 | Sugerman et al. . |
| 4,663,147 | | 5/1987 | DePrince . |
| 4,753,652 | | 6/1988 | Langer, et al. . |
| 4,871,376 | * | 10/1989 | DeWald . |
| 5,064,877 | | 11/1991 | Nass, et al. . |
| 5,372,796 | | 12/1994 | Wellinghoff . |
| 5,401,528 | | 3/1995 | Schmidt . |
| 5,472,491 | * | 12/1995 | Duschek et al. . |
| 5,519,088 | * | 5/1996 | Itoh et al. . |
| 5,720,805 | | 2/1998 | Wellinghoff et al. . |
| 6,022,404 | | 2/2000 | Ettlinger et al. . |

FOREIGN PATENT DOCUMENTS

| 0722992A1 | 12/1995 | (EP) . |
|---|---|---|
| WO92/16183 | 10/1992 | (WO) . |
| WO94/16129 | 7/1994 | (WO) . |
| WO99/17716 | 4/1999 | (WO) . |

* cited by examiner

Primary Examiner—Susan W. Berman
(74) Attorney, Agent, or Firm—Paula D. Morris & Associates, P.C.

(57) ABSTRACT

Zirconium oxide nanoparticles having at least some surface acid sites functionalized with a silanating agent and at least some surface acid sites finctionalized with zirconate or a zircoaluminate. The nanoparticles are useful in composites comprising photopolymerizable alkene matrix monomers, and are primarily suitable for dental and medical restoration.

29 Claims, No Drawings

MECHANICALLY STRONG AND TRANSPARENT OR TRANSLUCENT COMPOSITES MADE USING ZIRCONIUM OXIDE NANOPARTICLES

The U.S. government has certain rights in this invention pursuant to grant number NIDCR 1 P01 DE11688.

The present invention relates to alkene finctionalized zirconium oxide nanoparticle composites with polymerizable alkene matrix monomers. The composites are primarily suitable for dental and medical restoration; however, optical resins for use in high refractive index applications such as eyeglasses, resins for advanced prototyping, and adhesive applications also are possible.

BACKGROUND OF THE INVENTION

Colloidal silica nanoparticles currently are used as fillers in "microfilled" composite dental restorative resins. These particles can increase the hardness and wear resistance of photocured matrix polymers; however, the particles are not radiopaque and cannot be homogeneously dispersed within the matrix resin because of interparticle associations. The resulting coagulation leads to a substantial increase in viscosity and a consequent decrease in composite workability. This places a severe limitation on the practical filler loading in "microfilled" composites.

The loading problem can be partially offset by incorporating prepolymerized organic fillers into the resin in which a relatively high level of colloidal silica is incorporated into highly crosslinked polymeric granules. The workability of the composite resins containing these fillers is maintained, and the cure shrinkage is somewhat reduced. However, the fillers also yield failure prone interfaces and cause a high degree of light scattering, thereby limiting the depth of cure.

Photocurable dental repair materials are needed which are transparent or translucent, radioopaque, have good workabililty, and have good mechanical strength and stability.

SUMMARY OF THE INVENTION

The present invention provides a composition photopolymerizable into transparent or translucent solids comprising a matrix comprising monomers comprising a photopolymerizable unsaturated carbon-carbon bond, particles comprising zirconium oxide, the particles having a diameter in nanometers which is small enough to provide sufficient transparency but large enough to provide effective fracture toughness after photopolymerization, wherein the particles comprise a surface comprising hydroxyl groups, a first portion of the hydroxyl groups being bonded to a silicon atom of a silanating agent effective to increase hydrophobicity of the surface in an amount sufficient to allow the particles to be homogeneously dispersed in a hydrophobic resin, a second portion of the hydroxyl groups being bonded to a functionality selected from the group consisting of a zirconium atom of a photopolymerizable, hydrolyzable zirconate, and a zirconium atom or an aluminum atom of a photopolymerizable zircoaluminate.

DETAILED DESCRIPTION OF THE INVENTION

The present invention involves the discovery that photocurable resins which are radioopaque,which have good workability, and which are mechanically strong and stable may be made using nano-sized particles ("nanoparticles") comprising zirconium functionalized with photopolymerizable, hydrolyzable zirconates.

The zirconium based nanoparticles may be prepared by water hydrolysis of zirconium alkoxides, preferably normal zirconium alkoxides having from about 1 to about 3 carbon atoms. A preferred zirconium alkoxide is zirconium propoxide. If desired, the cluster synthesis may be enhanced using a suitable acid, preferably formic acid, as described in U.S. Pat. No. 5,372,796 to Wellinghoff, incorporated herein by reference.

Hydrolysis without using formic acid enhancement preferably takes place in the presence of excess alcohol as a diluent, preferably ethanol or propanol, most preferably n-propanol, in the presence of an inert gas, preferably nitrogen gas. Small droplets of water for hydrolyzing the zirconium alkoxide preferably are progressively added to the solution while stirring. The water droplets also preferably are diluted to a concentration of from about 1% (w/w) to about 3% (w/w) in a lower alcohol having from about 1 to about 3 carbon atoms, preferably propanol. In order to fully hydrolyze the zirconium alkoxide, the amount of water added must be twice the molar amount of the zirconium alkoxide unless the hydrolysis is enhanced using formic acid. During the addition of the water droplets, the solution is stirred vigorously. Typically, the addition of acid to produce a pH of about 3 is sufficient to form an adequate dispersion of zirconia clusters. Substantially any acid having a pH of less than about 3 may be used for this purpose, suitable acids including but not necessarily limited to nitric acid, hydrochloric acid, sulfuric acid, and the like. The chemical stoichiometry is as follows:

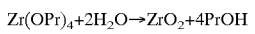

$$Zr(OPr)_4 + 2H_2O \rightarrow ZrO_2 + 4PrOH$$

In a preferred embodiment, a suitable organic acid is used to increase the rate of hydrolysis and to increase the amount of positive surface charge on the resulting zirconia clusters while producing only volatile byproducts. Any organic acid may be used as long as the ester resulting from the reaction has a low vapor pressure such that the ester will evaporate below about 200° C. In this embodiment, an amount of acid (preferably concentrated formic acid) which is about 1 to about 2 times the molar quantity of the alkoxide is added to the solution after adding the water/alcohol mixture. The solution is stirred for a prolonged period of from about 1 hour to about 24 hours, preferably about 12 hours. The reaction proceeds as follows:

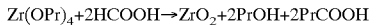

$$Zr(OPr)_4 + 2HCOOH \rightarrow ZrO_2 + 2PrOH + 2PrCOOH$$

When formic acid is used, the resulting clusters tend to grow large enough to scatter visible light, thereby giving the stirred solution a milky white appearance. If a smaller average cluster size is desired, then the system may be further acidified to a pH of near 1 by adding a strong acid, such as hydrochloric or nitric acid, in order to partially digest the clusters. The solution is stirred until achieving a desired average cluster size, preferably from about 20 nm to about 100 nm. The cluster size is measured using transmission electron microscopy (TEM), atomic force microscopy (AFM), or simple visual inspection based upon known light scattering phenomenon.

Assuming perfect bonding between the particle and matrix, a decrease in particle size at a given volume fraction of particles will increase the elastic constraint on the deforming matrix molecules and lead to an increase in modulus. However, as the particle size approaches molecular dimensions, the very closely spaced crosslinking points of high functionality within the matrix will substantially quench any large scale molecular motions. It is these motions which are important for energy dissipation and fracture toughness. Thus, for the purposes of this invention, particle sizes of from about 10 nm to about 150 nm are suitable, with particle sizes of about 100 nm generally being preferred. The clusters preferably have a diameter in nanometers which is small enough to provide sufficient transparency but large enough to provide effective fracture toughness after photopolymerization.

Once the desired average cluster size is achieved through adjustment of the solution pH, the clusters are organofunctionalized with an organofunctional coupling agent. The ideal organofunctional coupling agent readily and irreversibly condenses with the surface of the zirconia clusters and also provides double-bond functionality to the clusters to permit the clusters to copolymerize with a suitable surrounding organic matrix resin. Suitable organofunctional coupling agents for zirconia clusters include, but are not necessarily limited to photopolymerizable groups, such as vinyl, acryl, epoxy, or methacryl groups. Preferred organofunctional groups which maximize the mechanical strength of the resulting composite are hydrolyzable zirconates having the following general structure:

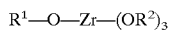

wherein $R^1$ is selected from the group consisting of hydrolyzable alkyl groups having 1 or more carbon atoms, said alkyl groups being effectively eliminatable from the system as free molecules either by volatilization or by isolated copolymerization within the organic matrix resin, and $R^2$ is selected from the group consisting of copolymerizable alkene substituents containing 2 or more carbon atoms. $R^1$ generally may be eliminated by volatilization if the number of carbon atoms is less than 9. Preferred organofunctional groups are neopentyl (diallyl) oxy trimethacryl zirconates and neopentyl (diallyl) oxy triacryl zirconates (described in U.S. Pat. No. 4,623,738, incorporated herein by reference).

Zircoaluminates having the following general structure also are preferred as organofunctional groups for zirconia clusters:

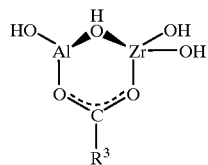

wherein $R^3$ is selected from the group consisting of copolymerizable alkene groups and carboxyfunctional substituents containing 3 or more carbon atoms, respectively. Preferred zircoaluminates are methacryloxy zircoaluminates (described in U.S. Pat. Nos. 4,539,049 and 4,539,048, both of which are incorporated herein by reference).

The required amount of organofunctional coupling agent may vary from about 0.1 to about 0.3 times the molar content of zirconium oxide in the ceramer. Quantities on the order of 0.2 times the molar content of zirconium oxide have been used to produce strong ceramers using dimethacrylate resins.

In order to organofunctionalize the clusters, the coupling agents are diluted with an excess of a suitable diluent, preferably an alcohol having from about 1 to about 3 carbon atoms, most preferably propanol, and added to the alcohol-zirconia-cluster solution. It is beneficial to maintain the acidity of the solution at a pH of from about 1 to about 3, preferably at about 3, in order for the reaction between the zirconia clusters and the primary coupling agent to be both timely and effective. The acidity may be maintained by adding a suitable inorganic acid, such as nitric acid. The resulting solution then is agitated, preferably by stirring, for a prolonged period of time, preferably at room temperature or ambient temperature, in order to accomplish the organofunctionalization. A typical stirring time is about 3 days.

After the primary organofunctionalization has taken place, the zirconia clusters may be left in the alcohol solution for further treatment. Alternately, if the solids yield is to be assessed, the clusters may be dried by vacuum evaporation, weighed, and the clusters may be redissolved in one of the lower alcohols, preferably methanol, at a later time. In either case, it is necessary to add a secondary, highly mobile surface agent that is able to increase the hydrophobicity of the cluster surfaces. Suitable secondary surface agents include, but are not necessarily limited to silanating agents. Preferred silanating agents are silanes bearing substituents selected from the group consisting of: from about 1 to about 2 alkyl groups having from about 1 to about 3 carbon atoms; from about 1 to about 2 alkylene groups; and, a substituent selected from the group consisting of chlorine, bromine, and an alkoxy group having from about 1 to about 3 carbon atoms. Preferred silanating agents have substituents selected from the group consisting of: one alkenyl group; two alkyl groups having from about 1 to about 3 carbon atoms; and, one alkoxy group having from about 1 to about 3 carbon atoms. A most preferred secondary surface agent is dimethyl ethoxy vinyl silane (DMEOVS) (U.S. Pat. No. 4,504,231, incorporated herein by reference). DMEOVS has the benefit of increasing the double bond density of the cluster surfaces while also being volatile enough that excessive amounts can be easily removed from the system. Nevertheless, the agent's greatest value is its ability to displace as many hydroxyl groups from the zirconia surfaces as possible and then to remain in place long enough to allow the particles to be homogeneously dispersed in a highly hydrophobic resin.

Any existing acid in the system will stabilize the silane against oligomerization and will catalyze its reaction with the cluster surfaces. Therefore, it is preferable to further acidify the solution to a pH of from about 1 to about 2, preferably to about 2, by adding a suitable inorganic acid, such as nitric acid. The resulting solution is again agitated, preferably by stirring at ambient conditions, for a prolonged period of time, typically from about 4 days to about 2 weeks.

Once the secondary coupling agent has been given sufficient time to react with the zirconia surfaces (at least 4 days), any acid (such as HCl) remaining in the solution may be removed by an acid scavenger. Any insoluble portion (generally less than 10% by weight) is removed by centrifugation, and any free protons in solution (such as HCl) are scavenged. Substantially any suitable acid scavenger may be used, such as polyamines and their copolymers. A preferred acid scavenger is polyvinyl pyridine. Using this acid scavenger, the system pH is adjusted upward to at least about 5, but not more than about 6. The supernatant solution is postreacted with a large excess of the secondary surface active agent in order to displace any hydroxyl groups remaining on the particle surfaces. If clouding of the solution occurs during postreaction, it may be desirable to centrifuge a second time and postreact again with an excess of the secondary surface active agent.

The functionalized nanoparticles then are ready to be mixed with the matrix monomers. Generally, a solution of from about 10 wt % to about 30 wt % of zirconium oxide nanoparticles in lower alcohol, preferably methanol, is mixed with a solution of a suitable matrix monomers. It is possible that a higher wt % of zirconium oxide nanoparticles also may be used. Suitable matrix monomers include, but are not necessarily limited to glycerol monomethacrylate, glycerol dimethacrylate, hydroxyethylmethacrylate (HEMA), 2,2-bis[p-(2'-hydroxy-3'-methacryloxypropoxy)phenylene] propane ("Bis-GMA), or ethoxylated bis-GMA and various blends of these monomers in combination with known plasticizers and photoinitiators or photoactivators. Known plasticizers include, but are not necessarily limited to triethyleneglycol dimethacrylate, and polypropylene oxide monomethacrylate. Known photoinitiators and photoactivators include, but are not necessarily limited to camphorquinone and 2-n-butoxyethyl-4-(dimethylamino) benzoate.

Since dimethacrylate resin monomers are soluble in the lower alcohols, it is convenient to add these resins directly to the existing zirconia solution, mixing them thoroughly. This liquid state mixing approach assures that all particles have sufficient opportunity to intimately adhere to the resin monomers. Once the mixture becomes homogeneous, the volatile agents may be directly removed by vacuum evaporation, yielding a single phase composite resin. Alternately, the resulting polymer may be isolated by filtration and/or centrifugation. If the hydroxyl groups at the surface of the zirconia clusters are thoroughly displaced, the zirconia clusters will not tend to interact with one another or agglomerate, even at near-neutral pH, once incorporated into a hydrophobic resin. Experimental samples contained 10, 20 and 30 wt % nanoparticle loadings.

The hydrophobicity of the nanoparticle can be increased by increasing the number of functionalized Zr—OH bonds. The ability to alter the surface of the nanoparticle in a controlled manner permits control of the working time of the unpolymerized composite and modification of the cured microphase structure of the composite material.

For example, if a hydrophobic, matrix monomer and hydrophilic nanoparticles are dissolved in a common hydrophilic solvent, evaporation of the solvent will yield an initially mobile fluid which rapidly will phase separate to form an elastic gel. Elastic properties are generated by an interpenetrating network phase of hydrophilic metal oxide nanoparticles within the hydrophobic matrix. If, on the other hand, the hydrophobic matrix monomer and the relatively hydrophobic nanoparticles are mixed in a common solvent and the solvent is evaporated, microphase separation will proceed more slowly providing increased working or storage time in the mobile state. With increased working time, the kinetic development of phase separation can be terminated at different stages by polymerization of the matrix monomer or prepolymer. Interconnectedness of the oxide network can have a strong influence on mechanical, permeability and electrical conductivity of the material.

By appropriate matching of the surface properties of the nanoparticles and the matrix monomer, it is possible to make a one phase system or generate a very fine phase separation that is insufficient to scatter light. This is of specific importance in many applications because several millimeters in thickness of such a material can be uniformly photocured to a solid. In addition, opacifying particles can be added to the transparent base for control of cosmetic features.

The invention will be better understood with reference to the following examples, which are set forth for purposes of illustration only:

EXAMPLE 1
ZrO$_2$ Cluster Synthesis by Aqueous Hydrolysis

A solution of 10.8367 g of 70% (w/w) zirconium propoxide in propanol was added to a round-bottom flask under nitrogen gas reflux to yield $2.32 \times 10^{-2}$ moles of the pure alkoxide. The solution was diluted by further adding 60 ml normal propanol while stirring with a magnetic stir bar. To completely hydrolyze the alkoxide, the amount of water added was twice the molar amount of zirconium propoxide, i.e. $4.63 \times 10^{-2}$ mole. 0.84 ml water was diluted with 40 ml normal propanol, and this solution was added to the flask dropwise (by burette) while stirring vigorously. The solution gradually became cloudy as the water was added. In order to increase the rate of hydrolysis, the solution was slightly acidified by adding 0.16 ml concentrated nitric acid to the flask. The solution clarified somewhat, remaining slightly hazy. Stirring was continued for about 2 hours. 2.3 ml ($\sim 4.63 \times 10^{-2}$ mol.) of pure neopentyl(diallyl) methacryl zirconate was diluted in 10 ml propanol and the resulting solution was added to the flask dropwise (by pipette), and the solution was stirred for 2 more hours. The system was then further acidified by adding 0.9 ml concentrated nitric acid, resulting in a system pH of about 3. Stirring was continued for about 3 days.

After stirring for 3 days, the flask was evacuated by pumping until only a dry powder remained. The powder was weighed and determined to have a mass near 6.3 g. The powder then was dissolved in methanol with the aid of a vortex mixer until the solids concentration was in the range of 10–20% (w/w). 15.3 ml ($\sim 9.26 \times 10^{-2}$ mol.) of pure dimethyl ethoxy vinyl silane was added to the solution. To prevent polymerization of the silane over time, the solution was further acidified by adding 0.7 ml concentrated nitric acid, resulting in a system pH of about 2. Stirring was continued for one week, and the solution was then neutralized with about 5 g polyvinyl pyridine (2% crosslinked) such that the system pH was greater than 5 but no more than 6. The polymeric base was isolated by filtering the solution.

Once the powder has been solvated, cluster concentration is known and is assumed to remain constant during neutralization. This assumption has been confirmed by re-drying aliquots of the solution. Any and all dilutions preferably are recorded.

EXAMPLE 2
ZrO$_2$ Cluster Synthesis Enhanced by Formic Acid 10.3540 g of 70% (w/w) zirconium propoxide solution was added to a round-bottom flask under nitrogen gas reflux. The solution was diluted with 60 ml normal propanol while stirring with a magnetic stir bar. 0.4 ml water was diluted in 20 ml normal propanol, and this solution was added to the flask dropwise (by burette) while stirring vigorously. The solution became slightly cloudy after the water was added. Stirring was continued for approximately 12 hours, and 1.25 ml concentrated formic acid was added. The resulting solution was stirred for at least 30 minutes, and then 2 ml concentrated hydrochloric acid was added, reducing the system pH to nearly 1. Once the solution was clarified to the point of being only slightly hazy, 2.2 ml of pure neopentyl (diallyl) methacryl zirconate was diluted in 10 ml propanol and added to the flask dropwise (by pipette). Stirring was continued for at least 2 hours, and the solution was pump vacuum dried to a powder.

The resulting powder was dissolved in methanol with the aid of a vortex mixer until the solids concentration was in the range of 10–20% (w/w). 14.6 ml of pure dimethyl ethoxy vinyl silane was added to the solution and the solution was stirred for one week. 4–5 g polyvinyl pyridine (2% crosslinked) was added while monitoring the system pH until it was between 5 and 6. The polymeric base was isolated by centrifugation.

EXAMPLE 3
Composite Formation Using Zirconia Clusters 14.7783 g of a solution having a concentration of clusters of 10.15% (w/w) was added to a round-bottom flask, yielding 1.50 g clusters. Added to this solution, and mixed thoroughly, was 6.00 g of a blend of 37 wt % bis-GMA, 25 wt % tetra ethylene glycol dimethacrylate (TEGDMA), 37.5 wt % bis-EMA (an ethoxylated version of bis-GMA) with 0.2% camphorquinone and 0.3% 2-n-butoxyethyl-4-(dimethylamine)benzoate (CQ/amine) (photoinitiator for on-demand polymerization).

The flask was evacuated after mixing in order to remove the volatile methanol and silane from the system. The yield was 7.50 g of composite resin having a solids content of 20% (w/w). The mechanical properties (±1 standard deviation) of a variety of composite specimens prepared as indicated are given in the Table below:

The resin had a fluid consistency which was easily manually packed into transparent silicone molds in order to produce mechanical testing specimens for flexural and fracture toughness testing. Once filled, the specimen molds were centrifuged to aid in the removal of air bubbles prior to photocuring. Specimens were spot cured using a dental curing lamp ($\lambda$=470 nm, QHL 75, Dentsply) for a minimum of one minute at each location. The flexure specimens were 2.5×2.5×25 mm in size while the fracture toughness specimens were 8 mm square and less than 4 mm thick. The geometry and testing approach was taken from the ASTM E399 specification, although the specimen size is somewhat smaller than that recommended. The cured specimens were tested to failure, and the fracture surfaces were analyzed by optical microscopy.

| Mechanical Property | Unfilled Model Resin | 70% Silica-Filled Model Resin | 20% Zirconia Filled Model Resin (Formic Acid Used) | 20% Zirconia-Filled Model Resin (Inorganic Acid Used) |
|---|---|---|---|---|
| Breaking Stress (psi) | 15271.66 ± 1,695.98 | 18658.58 ± 2,185.93 | 38522.47 ± 1,804.53 | 21816.34 ± 1,995.32 |
| Flexural Modulus (GPa) | 2.36 ± 0.21 | 7.87 ± 0.53 | 15.73 ± 1.93 | 12.80 ± 1.08 |
| Fracture Toughness [ksi(in½)] | 0.4557 ± 0.0436 | 0.3711 ± 0.2033 | 0.4586 ± 0.0979 | — |

Preliminary TEM images revealed that the average particle size was probably much smaller than the expected ~100 nm value, which was consistent with the high optical transparency of the sample. The average flexural strength of the resins was as much as 251.8 MPa. The elastic modulus of the materials was as much as 15.73 GPa GPa. The fracture toughness did not deteriorate with filler loadings up to 30 wt %.

Many modifications and variations may be made to the embodiments described herein without departing from the spirit of the present invention. The embodiments described herein are illustrative only should not be construed as limiting the scope of the present invention.

We claim:

1. A composition photopolymerizable into transparent or translucent solids comprising:
    a matrix comprising monomers comprising a photopolymerizable unsaturated carbon-carbon bond;
    particles comprising zirconium oxide, said particles having a diameter in nanometers which is small enough to provide sufficient transparency but large enough to provide effective fracture toughness after photopolymerization;
    wherein said particles comprise a surface comprising hydroxyl groups, a first portion of said hydroxyl groups being bonded to a silicon atom of a silanating agent effective to increase hydrophobicity of said surface in an amount sufficent to allow said particles to be homogeneously dispersed in a hydrophobic resin, a second portion of said hydroxyl groups being bonded to a functionality selected from the group consisting of a zirconium atom of a photopolymerizable, hydrolyzable zirconate, and a zirconium atom or an aluminum atom of a photopolymerizable zircoaluminate.

2. The composition of claim 1 wherein said zirconate has the following general structure:

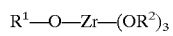

wherein $R^1$ is selected from the group consisting of hydrolyzable alkyl groups having 1 or more carbon atoms, said alkyl groups being effectively eliminatable as free molecules either by volatilization or by isolated copolymerization within said hydrophobic resin, and $R^2$ is selected from the group consisting of copolymerizable alkene substituents containing 2 or more carbon atoms; and said zircoaluminate has the following general structure:

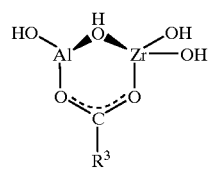

wherein $R^3$ is selected from the group consisting of copolymerizable alkene groups and carboxyfunctional substituents containing 3 or more carbon atoms, respectively.

3. The composition of claim 1 wherein said zirconate is selected from the group consisting of neopentyl(diallyl)oxy trimethacryl zirconates and neopentyl(diallyl)oxytriacryl zirconates; and said zircoaluminate is a methacryloxy-functional zircoaluminate.

4. A dental restoration comprising the composition of claim 1.

5. A resin for optical applications requiring a high refractive index comprising the, composition of claim 1.

6. An adhesive composition comprising the composition of claim 1.

7. A bone restoration comprising the composition of claim 1.

8. The composition of claim 1 wherein said silanating agent is a dialkyl alkoxy alkenyl silane wherein said alkyl groups and said alkoxy group have from about 1 to about 3 carbon atoms.

9. The composition of claim 1 wherein said silanating agent is dimethyl ethoxy vinyl silane.

10. A composition photopolymerizable into transparent or translucent solids comprising:
    a matrix comprising monomers selected from the group consisting of bisacrylate monomers, bis-methacrylate monomers, and combinations thereof;

particles comprising zirconium oxide, said particles having a diameter in nanometers which is small enough to provide sufficient transparency but large enough to provide effective fracture toughness after photopolymerization;

wherein said particles comprise a surface comprising hydroxyl groups, a first portion of said hydroxyl groups being bonded to a silicon atom of a silanating agent effective to increase hydrophobicity of said surface in an amount sufficent to allow said particles to be homogeneously dispersed in a hydrophobic resin, a second portion of said hydroxyl groups being bonded to a functionality selected from the group consisting of a zirconium atom of a photopolymerizable, hydrolyzable zirconate, and a zirconium atom or an aluminum atom of a photopolymerizable zircoaluminate.

11. The composition of claim 10 wherein said silanating agent is a dialkyl alkoxy alkenyl silane wherein said alkyl groups and said alkoxy group have from about 1 to about 3 carbon atoms.

12. The composition of claim 10 wherein said silanating agent is dimethyl ethoxy vinyl silane.

13. A composition photopolymerizable into transparent or translucent solids comprising:

a matrix comprising photopolymerizable monomers selected from the group consisting of bisacrylate monomers, bis-methacrylate monomers, and combinations thereof;

particles comprising zirconium oxide, said particles having a diameter in nanometers which is small enough to provide sufficient transparency but large enough to provide effective fracture toughness after photopolymerization;

wherein said particles comprise a surface comprising hydroxyl groups, a first portion of said hydroxyl groups being bonded to a silicon atom of a silanating agent effective to increase hydrophobicity of said surface in an amount sufficent to allow said particles to be homogeneously dispersed in a hydrophobic resin, a second portion of said hydroxyl groups being bonded to a functionality selected from the group consisting of a zirconium atom of a photopolymerizable, hydrolyzable zirconate, and a zirconium atom or an aluminum atom of a photopolymerizable zircoaluminate;

wherein said zirconate has the following general structure:

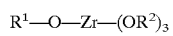

wherein $R^1$ is selected from the group consisting of hydrolyzable alkyl groups having 1 or more carbon atoms, said alkyl groups being effectively eliminatable as free molecules either by volatilization or by isolated copolymerization within said hydrophobic resin, and $R^2$ is selected from the group consisting of copolymerizable alkene substituents containing 2 or more carbon atoms; and said zircoaluminate has the following general structure:

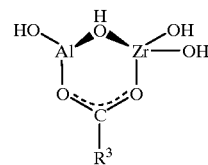

wherein $R^3$ is selected from the group consisting of copolymerizable alkene groups and carboxyfunctional substituents containing 3 or more carbon atoms, respectively.

14. The composition of claim 13 wherein said zirconate is selected from the group consisting of neopentyl(diallyl)oxy trimethacryl zirconates and neopentyl(diallyl)oxytriacryl zirconates; and said zircoaluminate is a methacryloxy-functional zircoaluminate.

15. The composition of claim 13 wherein said silanating agent is a dialkyl alkoxy alkenyl silane wherein said alkyl groups and said alkoxy group have from about 1 to about 3 carbon atoms.

16. The composition of claim 13 wherein said silanating agent is dimethyl ethoxy vinyl silane.

17. A composition photopolymerizable into transparent or translucent solids comprising:

a matrix comprising photopolymerizable monomers selected from the group consisting of glycerol monomethacrylate, glycerol dimethacrylate, hydroxyethylmethacrylate, 2,2-bis[p-(2'-hydroxy-3'-methacryloxypropoxy)phenylene]propane, ethoxylated 2,2-bis[p-(2'-hydroxy-3'-methacryloxypropoxy)phenylene]propane, and combinations thereof;

particles comprising zirconium oxide, said particles having a diameter in nanometers which is small enough to provide sufficient transparency but large enough to provide effective fracture toughness after photopolymerization;

wherein said particles comprise a surface comprising hydroxyl groups, a first portion of said hydroxyl groups being bonded to a silicon atom of a silanating agent effective to increase hydrophobicity of said surface in an amount sufficent to allow said particles to be homogeneously dispersed in a hydrophobic resin, a second portion of said hydroxyl groups being bonded to a functionality selected from the group consisting of a zirconium atom of a photopolymerizable, hydrolyzable zirconate, and a zirconium atom or an aluminum atom of a photopolymerizable zircoaluminate.

18. The composition of claim 17 wherein said zirconate has the following general structure:

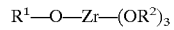

wherein $R^1$ is selected from the group consisting of hydrolyzable alkyl groups having 1 or more carbon atoms, said alkyl groups being effectively eliminatable as free molecules either by volatilization or by isolated copolymerization within said hydrophobic resin, and $R^2$ is selected from the group consisting of copolymerizable alkene substituents containing 2 or more carbon atoms; and said zircoaluminate has the following general structure:

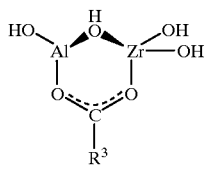

wherein $R^3$ is selected from the group consisting of copolymerizable alkene groups and carboxyfunctional substituents containing 3 or more carbon atoms, respectively.

19. The composition of claim 17 wherein said zirconate is selected from the group consisting of neopentyl(diallyl)oxy trimethacryl zirconates, neopeetyl(diallyl)oxytriacryl zirconates; and said zircoaluminate is a methacryloxy-functional zircoaluminate.

20. The composition of claim 17 wherein said silanating agent is a dialkyl alkoxy alkenyl silane wherein said alkyl groups and said alkoxy group have from about 1 to about 3 carbon atoms.

21. The composition of claim 17 wherein said silanating agent is dimethyl ethoxy vinyl silane.

22. A method of making photopolymerizable, transparent or translucent X-ray opaque compositions comprising admixing a matrix comprising monomers comprising a photopolymerizable unsaturated carbon-carbon bond with X-ray opaque zirconium oxide particles having a diameter in nanometers which is small enough to provide sufficient transparency and large enough to provide effective fracture toughness after photopolymerization, wherein said particles comprise a surface comprising hydroxyl groups, a first portion of said hydroxyl groups being bonded to a silicon atom of a silanating agent effective to increase hydrophobicity of said surface in an amount sufficent to allow said particles to be homogeneously dispersed in a hydrophobic resin, a second portion of said hydroxyl groups being bonded to a functionality selected from the group consisting of a zirconium atom of a photopolymnerizable, hydrolyzable zirconate, and a zirconium atom or an aluminum atom of a photopolymerizable zircoaluminate.

23. The method of claim 22 wherein said zirconate has the following general structure:

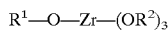

$$R^1\text{—O—Zr—}(OR^2)_3$$

wherein $R^1$ is selected from the group consisting of hydrolyzable alkyl groups having 1 or more carbon atoms, said alkyl groups being effectively eliminatable as free molecules either by volatilization or by isolated copolymerization within said hydrophobic resin, and $R^2$ is selected from the group consisting of copolymerizable alkene substituents containing 2 or more carbon atoms; and said zircoaluminate has the following general structure:

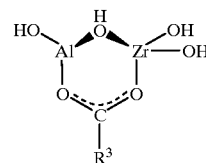

wherein $R^3$ is selected from the group consisting of copolymerizable alkene groups and carboxyfunctional substituents containing 3 or more carbon atoms, respectively.

24. The method of claim 22 wherein said zirconate is selected from the group consisting of neopentyl(diallyl)oxy trimethacryl zirconates, neopentyl(diallyl)oxytriacryl zirconates; and said zircoaluminate is a methacryloxy-functional zircoaluminate.

25. A method of making photopolymerizable, transparent or translucent X-ray opaque compositions comprising admixing a matrix comprising photopolymerizable monomers selected from the group consisting of bisacrylate monomers, bis-methacrylate monomers, and combinations thereof with particles comprising zirconium oxide, said particles having a diameter in nanometers which is small enough to provide sufficient transparency but large enough to provide effective fracture toughness after photopolymerization, wherein said particles comprise a surface comprising hydroxyl groups, a first portion of said hydroxyl groups being bonded to a silicon atom of a silanating agent effective to increase hydrophobicity of said surface in an amount sufficient to allow said particles to be homogeneously dispersed in a hydrophobic resin, a second portion of said hydroxyl groups being bonded to a functionality selected from the group consisting of a zirconium atom of a photopolymerizable, hydrolyzable zirconate, and a zirconium atom or an aluminum atom of a photopolymerizable zircoaluminate, wherein said zirconate has the following general structure:

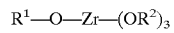

$$R^1\text{—O—Zr—}(OR^2)_3$$

wherein $R^1$ is selected from the group consisting of hydrolyzable alkyl groups having 1 or more carbon atoms, said alkyl groups being effectively eliminatable as free molecules either by volatilization or by isolated copolymerization within said hydrophobic resin, and $R^2$ is selected from the group consisting of copolymerizable alkene substituents containing 2 or more carbon atoms; and said zircoaluminate has the following general structure:

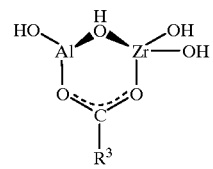

wherein $R^3$ is selected from the group consisting of copolymerizable alkene groups and carboxyfunctional substituents containing 3 or more carbon atoms, respectively.

26. The method of claim 25 wherein
said zirconate is selected from the group consisting of neopentyl(diallyl)oxy trimethacryl zirconates, neopentyl(diallyl)oxytriacryl zirconates; and
said zircoaluminate is a methacryloxy-functional zircoaluminate.

27. A method of making photopolymerizable, transparent or translucent X-ray opaque compositions comprising
providing a matrix comprising photopolymerizable monomers selected from the group consisting of glycerol monomethacrylate, glycerol dimethacrylate, hydroxyethylmethacrylate, 2,2-bis[p-(2'-hydroxy-3'-methacryloxypropoxy)phenylene]propane, ethoxylated 2,2-bis[p-(2'-hydroxy-3'-methacryloxypropoxy)phenylene]propane, and combinations thereof; and
mixing said matrix with particles comprising zirconium oxide, said particles having a diameter in nanometers which is small enough to provide sufficient transparency but large enough to provide effective fracture toughness after photopolymerization, wherein said particles comprise a surface comprising hydroxyl groups, a first portion of said hydroxyl groups being bonded to a silicon atom of a silanating agent effective to increase hydrophobicity of said surface in an amount sufficient to allow said particles to be homogeneously dispersed in a hydrophobic resin, a second portion of said hydroxyl groups being bonded to a functionality selected from the group consisting of a zirconium atom of a photopolymerizable, hydrolyzable zirconate, and a zirconium atom or an aluminum atom of a photopolymerizable zircoaluminate.

28. The composition of claim 27 wherein
said zirconate has the following general structure:

$$R^1-O-Zr-(OR^2)_3$$

wherein $R^1$ is selected from the group consisting of hydrolyzable alkyl groups having 1 or more carbon atoms, said alkyl groups being effectively eliminatable as free molecules either by volatilization or by isolated copolymerization within said hydrophobic resin, and $R^2$ is selected from the group consisting of copolymerizable alkene substituents containing 2 or more carbon atoms; and
said zircoaluminate has the following general structure:

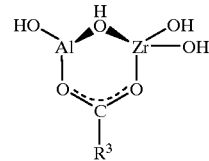

wherein $R^3$ is selected from the group consisting of copolymerizable alkene groups and carboxyfunctional substituents containing 3 or more carbon atoms, respectively.

29. The method of claim 27 wherein
said zirconate is selected from the group consisting of neopentyl(diallyl)oxy trimethacryl zirconates, neopentyl(diallyl)oxytriacryl zirconates; and
said zircoaluminate is a methacryloxy-functional zircoaluminate.

* * * * *

UNITED STATES PATENT AND TRADEMARK OFFICE
CERTIFICATE OF CORRECTION

PATENT NO.   : 6,194,481 B1
DATED         : February 27, 2001
INVENTOR(S)  : Benjamin R. Furman; Stephen T. Wellinghoff; Henry R. Rawls; Hong Dixon; Barry K. Norling It is certified that error appears in the above-identified patent and that said Letters Patent is hereby corrected as shown below:

Column 1,
Line 8, should read as follows:
The present invention relates to alkene functionalized Claim 5,
Should read as follows:
    A resin for optical applications requiring a high refractive index comprising the composition of claim 1.

Claim 19,
Should read as follows:
    The composition of claim 17 wherein said zirconate is selected from the group consisting of neopentyl(diallyl)oxy trimethacryl zirconates, neopenty(diallyl)oxytriacryl zirconates; and said zircoaluminate is a methacryloxy-functional zircoaluminate.

Signed and Sealed this

Twelfth Day of February, 2002

Attest:

JAMES E. ROGAN
Attesting Officer    Director of the United States Patent and Trademark Office